United States Patent [19]

Frost

[11] 4,245,651
[45] Jan. 20, 1981

[54] DETECTING BODY MOVEMENTS

[76] Inventor: James K. Frost, Spring House, Double Creek, Triabunna, Tasmania, Australia

[21] Appl. No.: 20,030

[22] Filed: Mar. 13, 1979

[51] Int. Cl.³ .............................................. A61B 5/08
[52] U.S. Cl. .................................. 128/721; 340/579; 340/667
[58] Field of Search ............... 128/782, 721, 722, 773, 128/774; 340/573, 665–667, 568

[56] References Cited

U.S. PATENT DOCUMENTS

| | | | |
|---|---|---|---|
| 3,631,438 | 12/1971 | Lewin | 128/721 |
| 4,066,072 | 1/1978 | Cummins | 128/782 |
| 4,146,885 | 3/1979 | Lawson, Jr. | 128/721 |

FOREIGN PATENT DOCUMENTS 2131047 12/1971 Fed. Rep. of Germany .......... 128/721

Primary Examiner—William E. Kamm
Attorney, Agent, or Firm—Larson, Taylor and Hinds

[57] ABSTRACT

An electro-mechanical transducer suitable for use in a cot or bed to detect body movements comprising a resiliently compressible assembly which emits noise while being compressed or expanded and a microphone for detecting the noise thus produced thereby to permit of the control of alarm or signal means.

The device is particularly designed to give warning of cessation of breathing movements of infants while asleep with the objective of reducing the incidence of so called "cot deaths".

15 Claims, 4 Drawing Figures

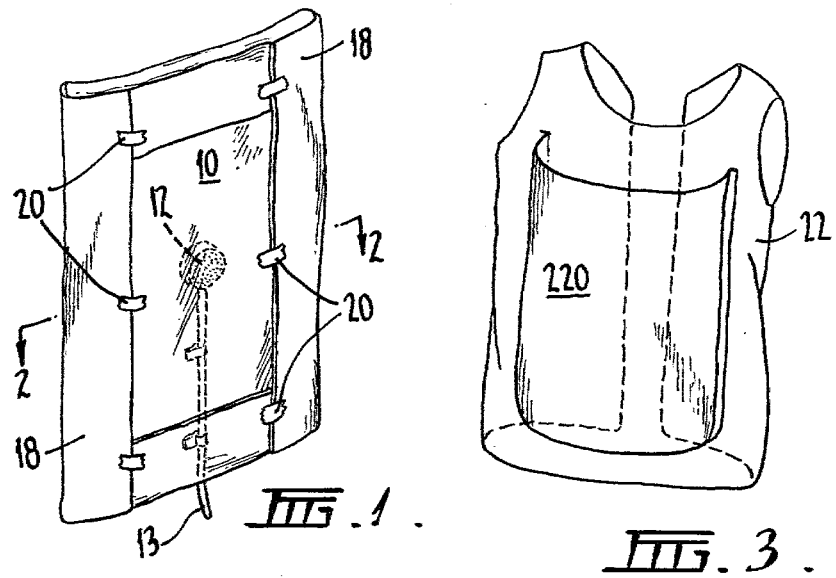
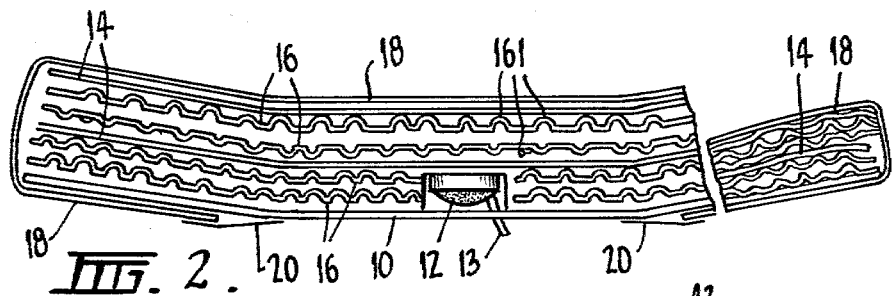
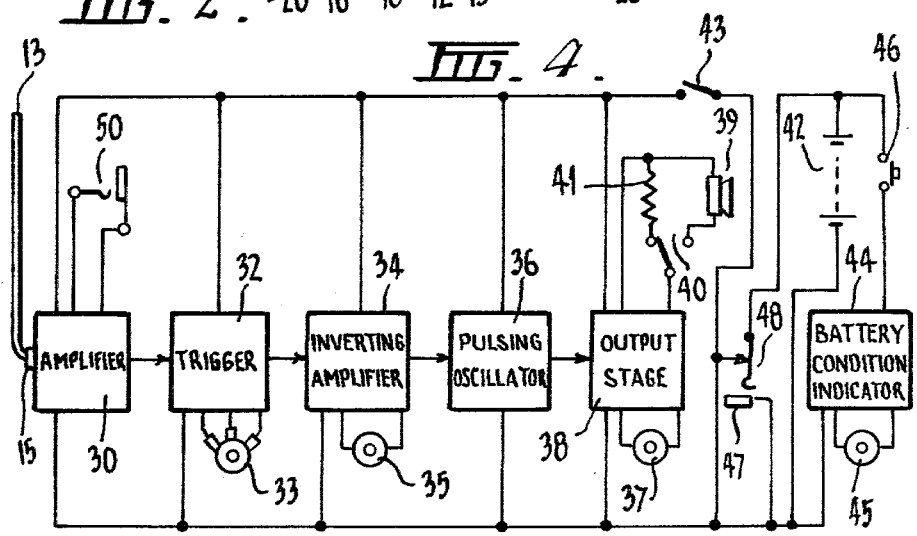

DETECTING BODY MOVEMENTS

This invention relates to apparatus for detecting body movements and to alarm or signal means controlled thereby and, while not restricted thereto, has been devised primarily with the objective of reducing the incidence of so-called "cot deaths" which now are a major component of the statistics of infant mortality during the first few months of life.

While the cause of cot deaths has not yet been clearly established, there are remedial measures which could be taken to prevent or reduce them if the parent or other person in charge of the infant, could quickly become aware that breathing had ceased. However, such deaths usually occur at night, unaccompanied by warning sounds, so that in many cases, some hours elapse before it is discovered that the infant has died.

For similar reasons apparatus, primarily intended for monitoring the breathing of a premature infant in a hospital incubator, and which is adapted to sound an alarm if breathing should cease, has already been devised, but such known apparatus is relatively complex and expensive and these disadvantages militate against its use in the home where most cot deaths occur.

It is therefore the general object of this invention to provide simple, convenient and relatively inexpensive means for detecting body movements, and to provide alarm or signal means for use in conjunction therewith.

Accordingly, in one aspect the invention provides an electro-mechanical transducer suitable for use in a cot or bed to detect body movements, especially movements of the chest wall, comprising a resiliently compressible assembly which emits noise while being compressed or expanded, and a microphone for detecting the noise thus produced thereby to permit of the control of alarm or signal means.

In use the microphone is connected in circuit with "hold-off" means which prevent activation of one or more associated alarm or signal devices while the transducer is producing substantially continuous noise. In the event however that such noise should cease for a predetermined short period, e.g., a period of several seconds, the said alarm device or devices, e.g., a lamp and/or a loudspeaker or bell, is or are automatically energized to alert the person in charge.

Thus an alarm circuit controlled by said hold-off means, may include a red signal lamp, and a loudspeaker while also means may be provided whereby other signal means, e.g., a green signal lamp, is automatically energized when the transducer is in use and is functioning normally.

In order however that the invention may be more fully understood, one preferred form thereof is hereinafter described with reference to the accompanying drawings in which:

FIG. 1 is a perspective view of a transducer responsive to breathing movements.

FIG. 2 is a sectional view in plan of the transducer and is drawn to an enlarged scale.

FIG. 3 is a perspective view of a jacket suitable for attaching the transducer to an infant; and FIG. 4 is a circuit diagram of one form of alarm apparatus for use in conjunction with the transducer.

Referring initially to FIGS. 1 and 2 the illustrated transducer comprises a freely compressible resilient pack which when suitable retained in contact with the chest wall of an infant is alternately compressed and expanded as the chest expands and contracts during inspiration and expiration respectively.

More particularly this pack comprises a rigid or semi-rigid back plate 10 of a size appropriate for the purpose, e.g., an approximately rectangular plate about 150 mm in length and 100 mm in width, this plate preferably having its longitudinal side edge portions bent forwardly as shown so that the plate is convex inwardly to conform approximately to the shape of the chest wall.

A microphone 12 secured centrally to the back plate so as to project forwardly therefrom is connected to the adjacent end of a suitable cable 13, e.g., a single screened cable, of the required length, and a jack plug 15 is attached to its opposite end. A plurality of layers 14 and 16 of different flexible sheet materials, which may be approximately of the same size as the plate, are arranged in front thereof these layers being retained in position by a flexible sheet 18 attached to the back plate. As shown in the drawing the foremost sheets 14 and 16 extend in front of the microphone, while the others are formed with clearance holes for the microphone.

More particularly the edges of the retaining sheet 18, which may be formed of aluminium foil or other suitable material, may be turned inwardly over and behind the back plate and then detachably secured thereto by strips 20 of adhesive tape, on in any other suitable manner.

The assembly thus formed is then preferably enclosed and sealed within a pouch (not shown) formed of P.V.C. or other suitable flexible and waterproof material which can readily be maintained in a clean and hygienic condition and for this purpose the initially open end of this pouch is preferably closed and sealed to, and at each side of, the cable 13.

The interior sheets designated 14 are composed of any suitable material, which emits crackling or rustling sounds while being bent or crumpled, e.g., regenerated cellulose of the kind which is well known under the registered trade mark "CELLOPHANE", or certain types of paper, while the illustrated interior sheets 16 may be composed of polythene or any other suitable flexible material and are formed with spaced projections, e.g., the illustrated dome-shaped or bubble-like projections 161. Sheet material of this kind is commercially available under the descriptive name "air bubble polythene".

Although for convenience in description the sheets 14 and 16 are shown in spaced apart relation in the left hand portion of FIG. 2, they are in fact necessarily disposed in contact as indicated at the right of the Figure. Thus the relative width of the pack is considerably exaggerated at the left of the Figure.

The air bubble polythene sheets 16 impart considerable resilience to the pack and the projections 161 thereon form spaced supports for the sheets 14 of regenerated cellulose. Thus as the pack is compressed the sheets 14 are bent around the numerous projections 161 and so produce the rustling and crackling sounds which are characteristic of that material, such sounds being also produced as the pack expands and the sheets 14 are returning towards their normal flat condition. Thus the noise produced within the pack is substantially continuous when the transducer is in use and the infant is breathing normally.

FIG. 3 shows a sleeveless jacket 22 by which the transducer may be conveniently attached to the infant, this jacket being formed with a pocket 220 to accommodate the transducer.

The signal apparatus diagrammatically shown in FIG. 4 may be constructed as a relatively small portable assembly so that it may be placed in any convenient position in the vicinity of a cot or bed and its principal components are, in sequence, a pre-amplifier 30 to which the transducer cable 13 is connected, an adjustable electronic trigger 32 connected to the pre-amplifier, an inverting amplifier 34, a pulsing oscillator 36 and an output stage 38. These several electronic components are individually well known to persons skilled in the art and so do no require further description.

The trigger 32 incorporates sensitivity adjustment means 33, which enable the noise threshold for its operation to be regulated, i.e. the minimum noise level at which it will transmit a signal to the inverting amplifier 34 which has no output to the pulsing oscillator 36 while it is receiving an input from the trigger, and vice versa. The inverting amplifier 34 preferably incorporates delay means which cause a predetermined delay, e.g., a delay of several seconds, in its response to the cessation of an input from the trigger after which it transmits an output to the pulsing oscillator 36 which then transmits a pulsed audio frequency signal to the output stage 38.

A "green" signal lamp 35 associated with the inverting amplifier 34 is arranged to be energised continuously when the apparatus is in use and is functioning normally, i.e., when an input is being received from the trigger 32, while a "red" signal lamp 37 associated with the output stage 38 is continuously energised if, while the apparatus is in use, a pulsed input is being received by the output stage due to the cessation of an input to the inverting amplifier from the trigger.

An audible alarm device, e.g., a speaker 39 is also preferably connected in circuit with the output stage and preferably through a manual switch 40 which may be a two-way switch which connects a dummy load 41 in circuit with the output stage when the speaker is switched off.

For reasons both of convenience and safety the apparatus is preferably energised by a storage battery 42, e.g., a six volt battery, which is connected in circuit with the apparatus by a manual switch 43. A battery condition indicator 44 incorporating a signal lamp 45, e.g. an "amber" lamp, is arranged to be connected in circuit with the battery by means of a normally open manual test switch 46, the condition indicator being preferably adjusted so as to indicate that the battery needs re-charging while it is still capable of operating effectively for a period which is sufficient to ensure that the unit will not fail during the night.

The battery is re-charged when required by plugging in a mains charger at 47 and insertion of the plug automatically opens a normally closed switch 48 in order to isolate the electronic assembly.

In use therefore the transducer may be attached to the infant, e.g., by means of the jacket 22, or placed below it in the cot or bed so that it is regularly compressed and expanded due to the breathing movements of the chest wall.

The connecting cable 13 is then connected to the electronic apparatus, which may be arranged in any suitable location and this unit is then connected to the battery by the switch 43 at which time the "green" signal lamp 35 will be energised.

However if breathing movements should cease for more than the predetermined period of several seconds, the inverting amplifier 34, which then is not receiving an input from the trigger, activates the pulsing oscillator 36 and the circuit of the "green" signal lamp 35 is broken.

The pulsing oscillator thus transmits a pulsed input to the output stage with the consequence that the "red" signal lamp 37 is energized as also is the speaker 42 when it is connected in circuit.

Consequently a parent or other person in charge of the infant receives visual and/or audible signals within a period of several seconds if breathing has apparently ceased so that appropriate remedial measures may quickly be instituted.

As indicated at 50 in FIG. 4, provision may also be made at the pre-amplifier for plugging in a monitor telephone or a sound recorder to enable the person in charge to listen to or record the breathing sounds as there is some evidence that either of these procedures may reveal breathing irregularities which could indicate a higher than normal degree of risk of cot death.

It will of course be understood that various alternative forms of electronic or other signal or alarm apparatus for use in conjunction with the transducer may readily be devised by persons skilled in the art while similarly the transducer may incorporate any materials or means which produce or cause to be produced, substantially continuous low level noise when the transducer is used in the manner hereinbefore described.

While the transducer described above and shown in the drawings is perferred it will be evident to persons skilled in the art that various other noise-emitting, resiliently compressible assemblies may be used in lieu thereof. For example, the aforesaid sheets of regenerated cellulose and polythene may be replaced by a filling comprising crumpled pieces of regenerated cellulose, paper of other material which has the characteristic of emitting noise while being bent or crumpled.

I claim:

1. An apnoea alarm system for use in a cot or bed to detect body movements comprising a back plate having a microphone supported thereon and projecting forwardly therefrom, a flexible cover attached to the back plate and extending in front thereof thereby to define an intervening space and a resiliently compressible packing arranged within said space, said packing comprising means, comprising a plurality of flexible sheets of material disposed generally parallel to the back plate, for emitting noise in response to being bent or crumpled, the microphone being arranged to detect the noise produced by said means to permit the control of an output means.

2. An apnoea alarm system according to claim 1, wherein a plurality of sheets of resiliently compressible material are disposed generally parallel to the back plate with at least one of said sheets of resiliently compressible material being arranged between two adjacent sheets of said flexible noise emitting material.

3. An apnoea alarm system according to claim 1, further comprising a pouch in which said said back plate, said cover and said packing are enclosed, said pouch being formed of a flexible, waterproof, hygienic material.

4. An apnoea alarm system according to claim 3, wherein said pouch is secured to a blanket arranged to be positioned underneath or around the occupant of the cot or bed.

5. An apnoea alarm system according to claim 3, wherein said pouch is secured to a vest to be worn by the occupant of a cot or bed.

6. An apnoea alarm system according to claim 3, wherein said pouch is formed of P.V.C.

7. An apnoea alarm system according to claim 1, including output means comprising an output device, means for activating said output device and hold-off means controlled by the said microphone for preventing activation of said output device while sound of a predetermined intensity is being received by the microphone.

8. An apnoea alarm system according to claim 7, including delay means for preventing activation of said output device until the lapse of a predetermined period during which sound of said predetermined intensity has not been received by the microphone.

9. An apnoea alarm system according to claim 7, wherein said hold-off means comprises an electronic trigger in circuit with an inverting amplifier which has no output while the trigger is receiving an input from the microphone and vice versa, and means controlled by the output from the inverting amplifier for causing said output device to be activated.

10. An apnoea alarm system according to claim 7, wherein the inverting amplifier is connected to an output stage thereby to transmit a pulsed audio frequency signal to the latter when the inverting amplifier has an output, thereby to cause said output device to be activated.

11. An apnoea alarm system according to claim 7, including connector means for enabling means for rendering the breathing sounds audible to be connected in the circuit.

12. An apnoea alarm system according to claim 7, including a storage battery for energizing said output means, means for indicating the condition of the battery, and switch means for isolating said output means from the battery consequent upon connecting recharging means in circuit therewith.

13. An apnoea alarm system according to claim 7, wherein said output device comprises an alarm.

14. An apnoea alarm system according to claim 7, wherein said output device comprises a signal means.

15. An apnoea alarm system according to claim 7 including connector means for enabling recording means for the breathing sounds to be connected in the circuit.

* * * * *